(12) United States Patent
Sakai et al.

(10) Patent No.: US 10,267,817 B2
(45) Date of Patent: Apr. 23, 2019

(54) AUTOMATIC ANALYSIS APPARATUS

(71) Applicant: Hitachi High-Technologies Corporation, Minato-ku, Tokyo (JP)

(72) Inventors: Tatsuya Sakai, Tokyo (JP); Akihisa Makino, Tokyo (JP); Minoru Sano, Tokyo (JP); Chie Yabutani, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 68 days.

(21) Appl. No.: 15/326,820

(22) PCT Filed: Jun. 10, 2015

(86) PCT No.: PCT/JP2015/066651
§ 371 (c)(1),
(2) Date: Jan. 17, 2017

(87) PCT Pub. No.: WO2016/017289
PCT Pub. Date: Feb. 4, 2016

(65) Prior Publication Data
US 2017/0212138 A1    Jul. 27, 2017

(30) Foreign Application Priority Data
Jul. 29, 2014  (JP) .................. 2014-153424

(51) Int. Cl.
*G01N 35/02*    (2006.01)
*G01N 35/00*    (2006.01)
(Continued)

(52) U.S. Cl.
CPC .......... *G01N 35/025* (2013.01); *G01N 33/86* (2013.01); *G01N 35/00* (2013.01);
(Continued)

(58) Field of Classification Search
None
See application file for complete search history.

(56) References Cited

U.S. PATENT DOCUMENTS

2008/0044912 A1*  2/2008  Yamamoto .......... G01N 21/272
                                                                  436/69
2008/0318323 A1   12/2008  Shintani et al.
(Continued)

FOREIGN PATENT DOCUMENTS

JP          7-270427 A       10/1995
JP          2001-13151 A      1/2001
(Continued)

OTHER PUBLICATIONS

International Search Report (PCT/ISA/210) issued in PCT Application No. PCT/JP2015/066651 dated Sep. 15, 2015 with English translation (5 pages).
Japanese-language Written Opinion (PCT/ISA/237) issued in PCT Application No. PCT/JP2015/066651 dated Sep. 15, 2015 (4 pages).
European Office Action issued in counterpart European Application No. 15828276.4 dated Oct. 19, 2018 (six (6) pages).

*Primary Examiner* — Kathryn Wright
(74) *Attorney, Agent, or Firm* — Crowell & Moring LLP

(57) ABSTRACT

Provided is an automatic analysis apparatus for inspecting blood coagulation, which is capable of miniaturizing device configuration and reducing device costs. The automatic analysis apparatus includes: a reaction container in which a specimen and a reagent are mixed with each other and the mixed solution is reacted; a sample dispensing mechanism which dispenses the specimen into the reaction container; a blood coagulation time measuring unit in which the reaction container is mounted to measure a coagulation time of the mixed solution within the reaction container; a reaction container accommodating unit which accommodates a plurality of reaction containers provided to the blood coagulation measuring unit; a reaction container transfer mechanism which grasps the reaction container and transfers the reac- (Continued)

tion container to the blood coagulation measuring unit; and a control unit which controls the reaction container transfer mechanism.

12 Claims, 12 Drawing Sheets

(51) Int. Cl.
*G01N 35/10* (2006.01)
*G01N 33/86* (2006.01)
*G01N 35/04* (2006.01)

(52) U.S. Cl.
CPC ... *G01N 35/00069* (2013.01); *G01N 35/0099* (2013.01); *G01N 35/04* (2013.01); *G01N 35/1002* (2013.01); *G01N 2035/0441* (2013.01); *G01N 2035/0453* (2013.01)

(56) References Cited

U.S. PATENT DOCUMENTS

| | | |
|---|---|---|
| 2012/0291872 A1 | 11/2012 | Brady et al. |
| 2015/0104351 A1 | 4/2015 | Makino et al. |
| 2015/0147230 A1 | 5/2015 | Yoshikawa et al. |
| 2015/0323557 A1* | 11/2015 | Tamezane .......... G01N 35/1009 422/67 |

FOREIGN PATENT DOCUMENTS

| | | |
|---|---|---|
| JP | 2013-250218 A | 12/2013 |
| WO | WO 2006/107016 A1 | 10/2006 |
| WO | WO 2013/187210 A1 | 12/2013 |
| WO | WO /2014/013836 * | 1/2014 |

* cited by examiner

[FIG. 1]
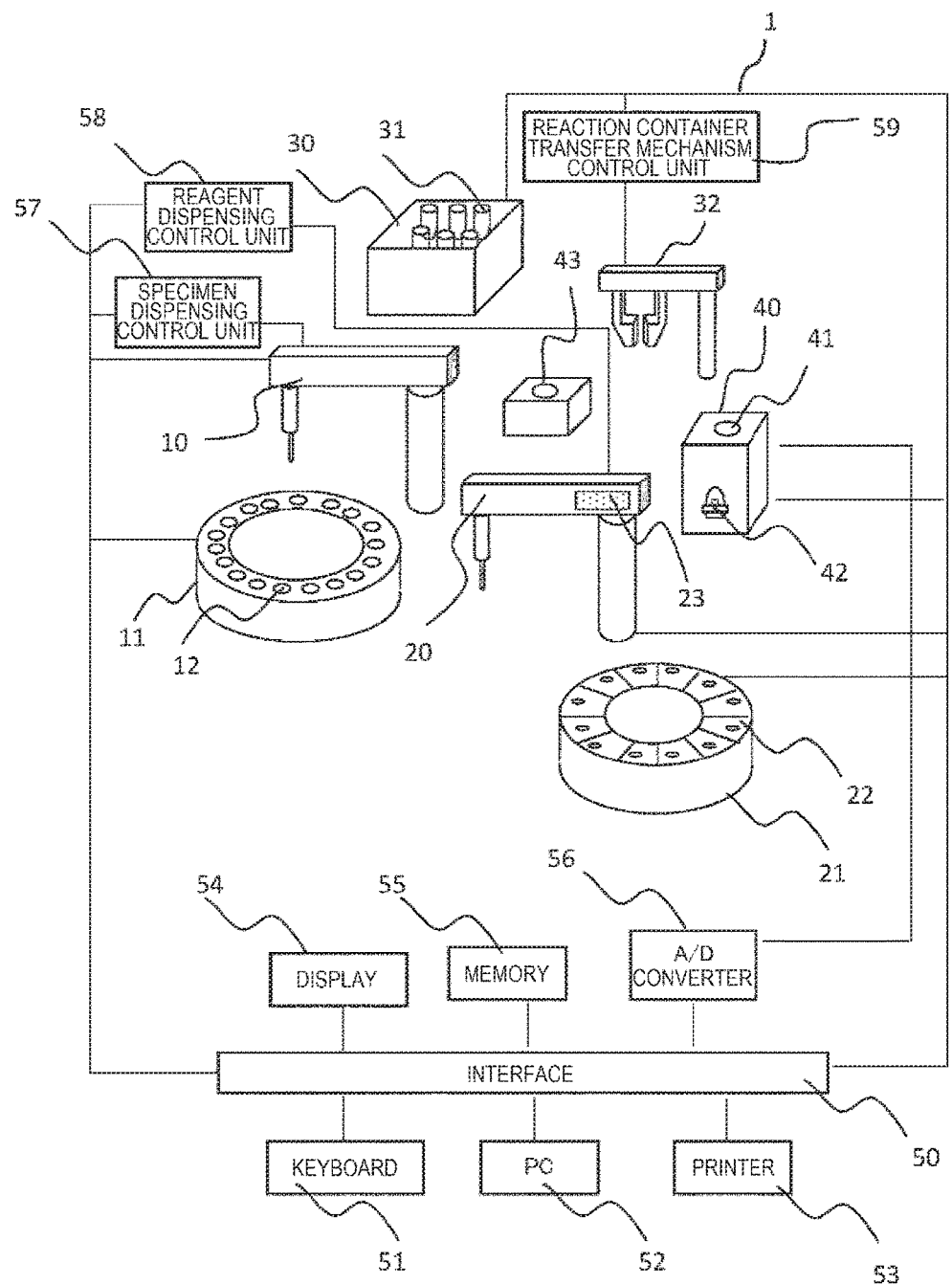

[FIG. 2]
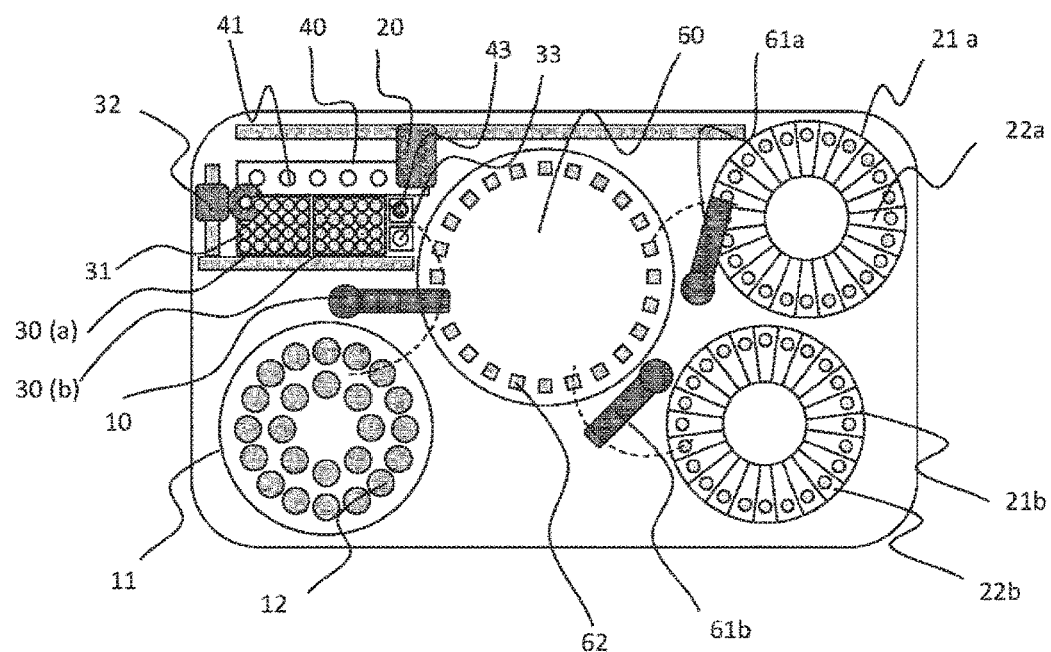

[FIG. 3]

(a) REACTION CONTAINER TRANSFER MECHANISM INITIAL POSITION
↓ REQUEST FOR ANALYSIS
(b) MOVE TO ABOVE REACTION CONTAINER ACCOMMODATING UNIT AND GRASP REACTION CONTAINER
↓
(c) TRANSFER AND MOUNT REACTION CONTAINER TO COAGULATION SPECIMEN DISPENSING UNIT
↓
(d) MOVE TO REACTION CONTAINER TRANSFER MECHANISM INITIAL POSITION
↓ SAMPLE DISPENSING MECHANISM DISPENSES SPECIMEN INTO REACTION CONTAINER
(e) MOVE TO ABOVE COAGULATION SPECIMEN DISPENSING UNIT AND GRASP REACTION CONTAINER CONTAINING SPECIMEN
↓
(f) TRANSFER AND MOUNT REACTION CONTAINER CONTAINING SPECIMEN TO COAGULATION TIME DETECTING UNIT
↓
(g) MOVE TO REACTION CONTAINER TRANSFER MECHANISM INITIAL POSITION

FIG. 4A

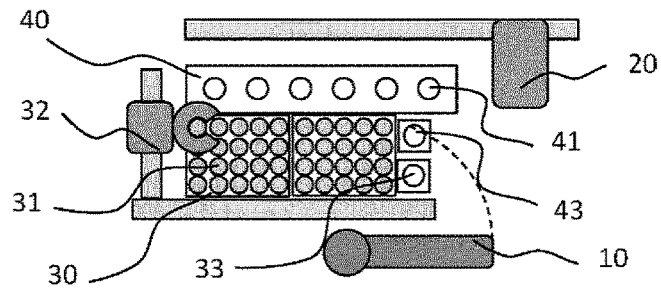

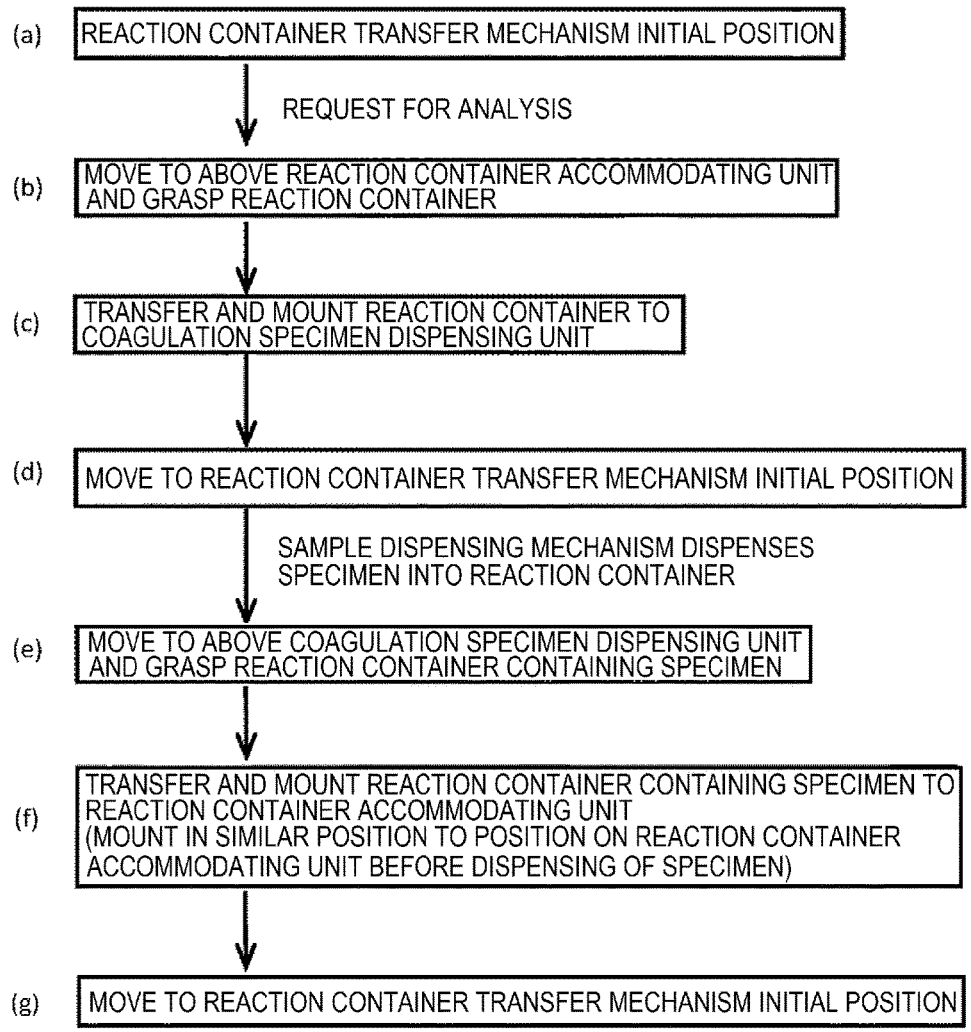
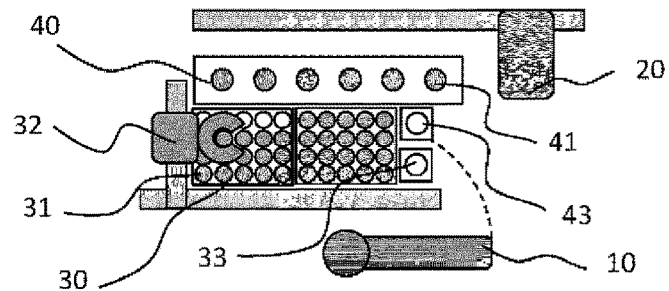
FIG. 6A

[FIG. 7]
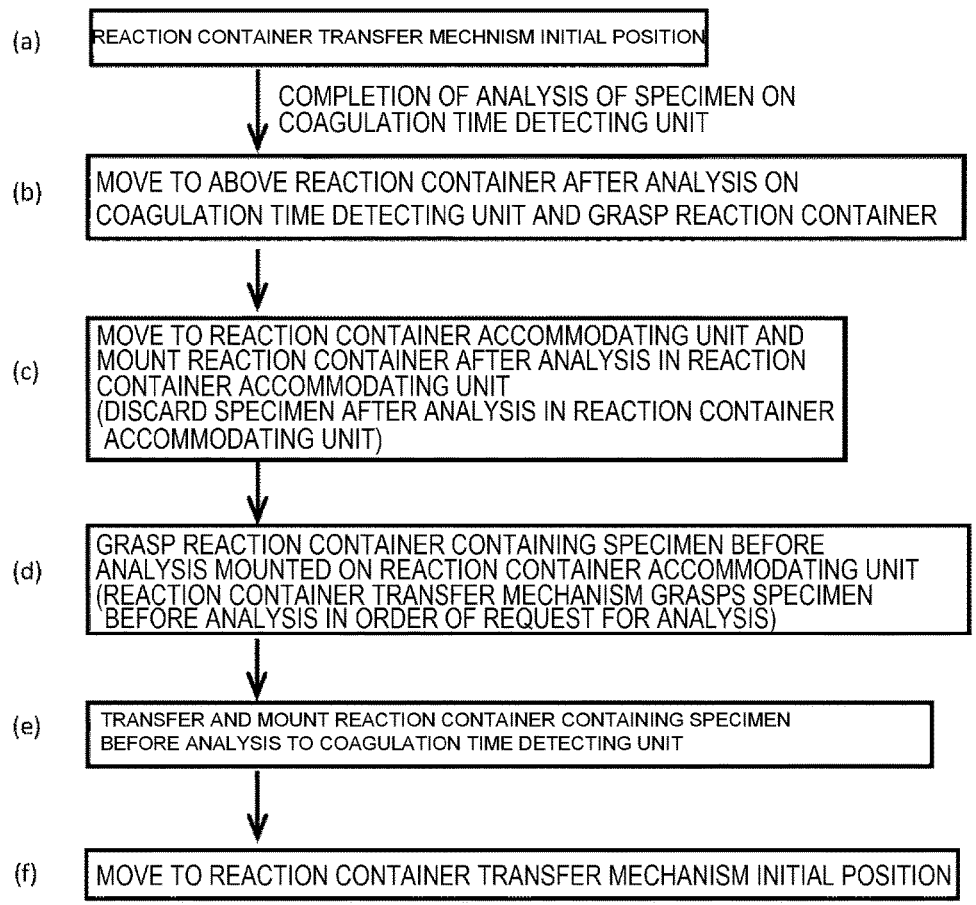
FIG. 8A
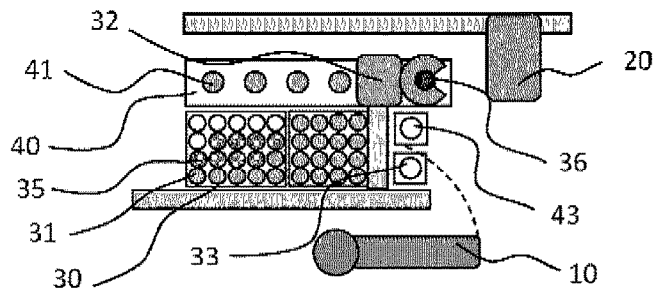

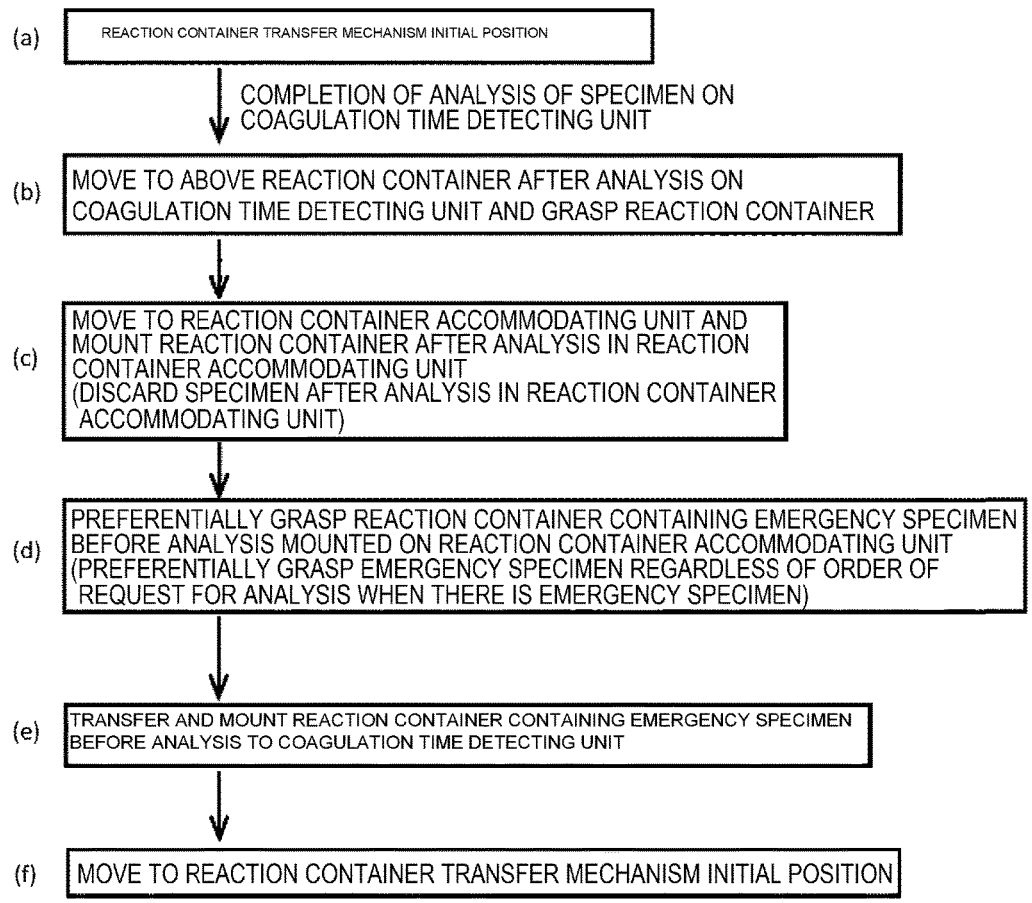
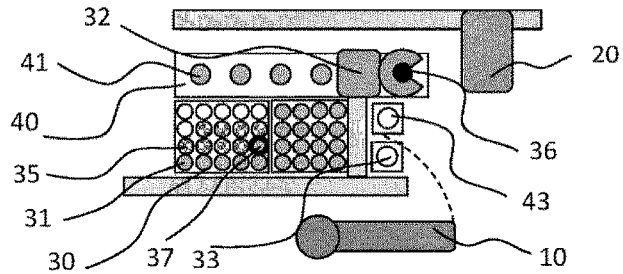
FIG. 10A

[FIG. 11]
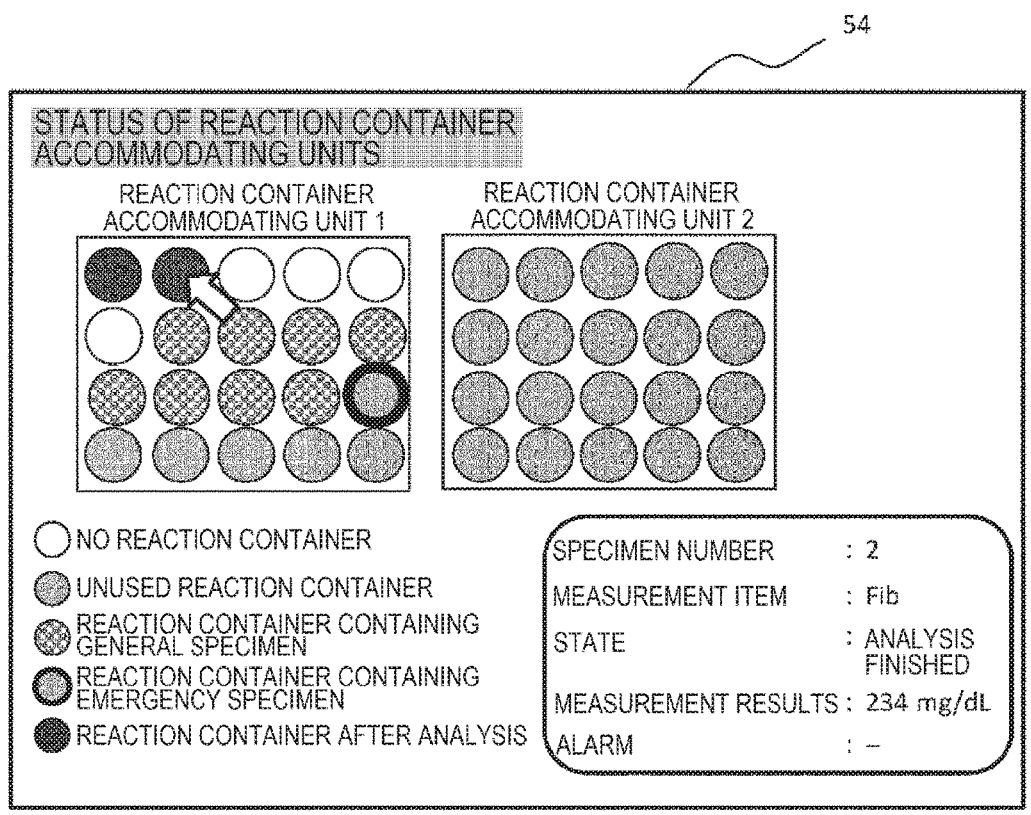

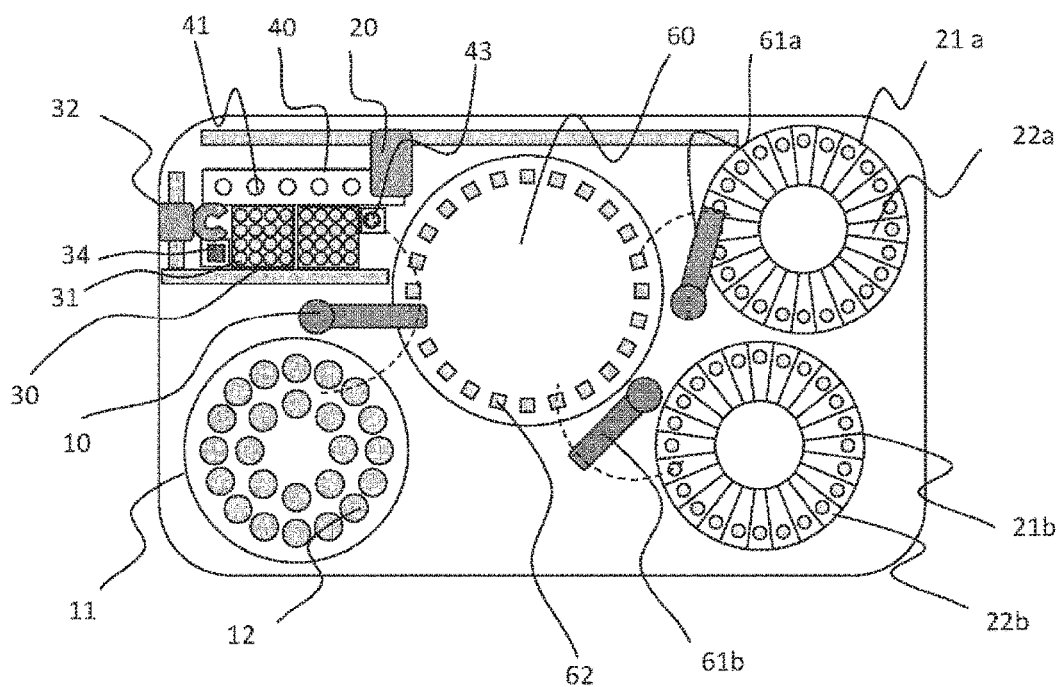
[FIG. 12]

AUTOMATIC ANALYSIS APPARATUS

TECHNICAL FIELD

The present invention relates to an automatic analysis apparatus for analyzing the amount of a component contained in a sample such as blood or urine.

BACKGROUND ART

Inspections of a specimen in the field of clinical tests include inspection of immune serum, biochemical inspection, inspection of blood coagulation and the like. These inspections have been conducted separately with specialized apparatuses, and it sometimes takes time for the installation of a specimen, the operation for requesting analysis in each apparatus, the check of the output results, the management of the results and the like.

Moreover, for inspection of blood coagulation, there are a method for detecting the period from the activation of a coagulation factor to the precipitation of fibrin optically or physically by examining the consistency and a method for detecting a marker involved in blood coagulation as a change in the quantity of the transmitted light. Thus, different detectors are required for the methods. Here, the former is called coagulation time measurement, and the latter is called absorbance measurement.

In view of the rapidness of the inspection and the simplification of the management of the apparatus, automatic analysis apparatuses capable of conducting a plurality of inspections with different measurement styles consistently have been provided. With respect to the biochemical automatic analysis apparatus described in PTL 1, a method for conducting a plurality of inspections by a common inspection mechanism is proposed to miniaturize the apparatus and to improve the efficiency. In this method, inspection of immune serum or biochemical inspection is conducted in the inspection area which is also used for inspection of blood coagulation. Moreover, PTL 2 discloses an automatic analysis apparatus capable of conducting biochemical inspection and inspection of blood coagulation.

CITATION LIST

Patent Literature

PTL 1: JP-A-2001-13151
PTL 2: WO2013/187210

SUMMARY OF INVENTION

Technical Problem

PTL 1 discloses a technique for inspecting coagulation by moving a plurality of reaction containers for inspecting blood coagulation at a constant speed. However, the system of mechanism is complex because a transfer path for moving the reaction containers has to be driven. Also, there is a problem of the increased size of the apparatus because the apparatus has a mechanism system for driving.

PTL 2 discloses an automatic analysis apparatus having a plurality of photometric ports. Because there is no driving mechanism system for blood coagulation measurement, the problem of PTL 1 can be solved. However, in the coagulation time measurement, the measurement times of the specimens vary, and some specimens take a long time for the measurement. Also, when many specimens are measured in the coagulation time measurement, the specimens stay, and the measurement of coagulation cannot always be conducted. Thus, specimens which should be dispensed remain on the sample disk, and the efficiency of dispensing decreases. In the technique of PTL 2, the staying of the specimens in the sample disk is not considered.

When many photometric ports for measuring many specimens are provided to solve the problems, the size of the apparatus becomes large. Also, the device costs become high because many light sources are required.

Therefore, an object of the invention is to provide an automatic analysis apparatus for inspecting blood coagulation which can prevent the decrease in the efficiency of dispensing specimens while miniaturizing device configuration or reducing device costs.

Solution to Problem

Representative inventions according to this application are as follows.

A representative invention is an automatic analysis apparatus, having: a sample dispensing mechanism that dispenses a specimen into a reaction container in which the specimen and a reagent are mixed with each other and in which the mixed solution is reacted; a blood coagulation time measuring unit in which the reaction container is mounted to measure a coagulation time of the mixed solution within the reaction container; a reaction container accommodating unit which accommodates a plurality of reaction containers provided to the blood coagulation measuring unit; a reaction container transfer mechanism which grasps the reaction container and transfers the reaction container to the blood coagulation measuring unit; and a control unit which controls the reaction container transfer mechanism: wherein the control unit controls the transferring and mounting of the reaction container, into which the specimen is dispensed, to the reaction container accommodating unit by means of the reaction container transfer mechanism.

Another representative invention is an automatic analysis apparatus, having: a sample dispensing mechanism that dispenses a specimen into a reaction container in which the specimen and a reagent are mixed with each other and in which the mixed solution is reacted; a blood coagulation time measuring unit in which the reaction container is mounted to measure a coagulation time of the mixed solution within the reaction container; a reaction container accommodating unit which accommodates a plurality of reaction containers provided to the blood coagulation measuring unit; a reaction container transfer mechanism which grasps the reaction container and transfers the reaction container to the blood coagulation measuring unit; and a control unit which controls the reaction container transfer mechanism: wherein the control unit controls the mounting of the reaction containers, into which a specimen is dispensed, in the blood coagulation time measuring unit by means of the reaction container transfer mechanism until the blood coagulation time measuring unit is filled with the reaction containers, the transferring and mounting of a reaction container containing a specimen before the measurement to the reaction container accommodating unit by means of the reaction container transfer mechanism when the blood coagulation time measuring unit is filled with the reaction containers and the mounting of the reaction container containing the specimen before the measurement mounted in the reaction container accommodating unit in the blood coagulation time measuring unit by means of the reaction container transfer mechanism when a space for a reaction container in the blood coagulation time measuring unit becomes vacant.

Advantageous Effects of Invention

According to the invention, an automatic analysis apparatus for inspecting blood coagulation which is capable of miniaturizing device configuration and reducing device costs can be provided. Moreover, even when a limited number of reaction containers cannot be analyzed at a time, specimens can be prevented from staying, and a decrease in the efficiency of dispensing specimens can be prevented. Problems, structures and effects other than those described above are explained in the following description of embodiments.

BRIEF DESCRIPTION OF DRAWINGS

FIG. 1 A system block diagram showing the whole structure of the automatic analysis apparatus capable of conducting blood coagulation measurement according to an embodiment of the invention.

FIG. 2 A schematic view of the automatic analysis apparatus capable of conducting blood coagulation measurement and biochemical measurement according to an embodiment of the invention.

FIG. 3 A figure summarizing an example of the operating sequence of the reaction container transfer mechanism 32 used when an operator has started the analysis of blood coagulation and a space in a coagulation time detecting unit 41 is vacant in an embodiment of the invention.

FIG. 4A A schematic view of an operation of the reaction container transfer mechanism 32 in the operating sequence shown in FIG. 3 in an embodiment of the invention.

FIG. 5 A figure summarizing an example of the operating sequence of the reaction container transfer mechanism 32 used when all the blood coagulation time detecting units 41 are used for the measurement in an embodiment of the invention.

FIG. 6A A schematic view of an operation of the reaction container transfer mechanism 32 in the operating sequence shown in FIG. 5 in an embodiment of the invention.

FIG. 7 The operating sequence of the reaction container transfer mechanism 32 used when the analysis of a reaction container 31 on a coagulation time detecting unit 41 is finished in an embodiment of the invention is shown.

FIG. 8A A schematic view of an operation of the reaction container transfer mechanism 32 in the operating sequence shown in FIG. 7 in an embodiment of the invention.

FIG. 9 The operating sequence of the reaction container transfer mechanism 32 used when there is a reaction container 37 containing an emergency specimen on a reaction container accommodating unit 30 in an embodiment of the invention is shown.

FIG. 10A A schematic view of an operation of the reaction container transfer mechanism 32 in the operating sequence shown in FIG. 9 in an embodiment of the invention.

FIG. 11 A figure showing an example of the screen which displays the state of the reaction containers 31 on the reaction container accommodating units 30 on the display 54 in an embodiment of the invention.

FIG. 12 A figure showing an example of a schematic view of the automatic analysis apparatus capable of conducting blood coagulation measurement and biochemical measurement according to an embodiment of the invention.

DESCRIPTION OF EMBODIMENTS

Figure 4B:
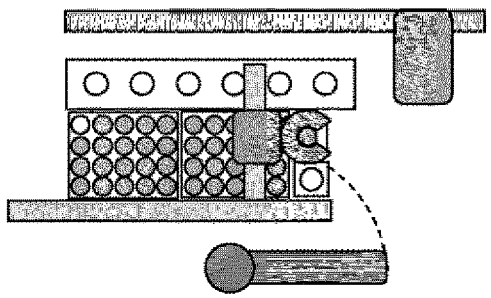
FIG. 4B A schematic view of an operation of the reaction container transfer mechanism 32 in the operating sequence shown in FIG. 3 in an embodiment of the invention.

Embodiments of the invention are explained based on the drawings below. In all the figures for explaining the embodiments, components having a same function are basically indicated by a same reference sign, and the repeated description thereof is avoided as much as possible.

FIG. 1 is a system block diagram showing the whole structure of an automatic analysis apparatus capable of conducting blood coagulation measurement which is the basis of an Example of the invention. As shown in FIG. 1, an automatic analysis apparatus 1 is mainly composed of a sample dispensing mechanism 10, a sample disk 11, a coagulation reagent dispensing mechanism 20, a reagent disk 21, a reaction container accommodating unit 30, a reaction container transfer mechanism 32, a coagulation time measuring unit 40 and a computer (control unit) 52.

The sample disk 11 is capable of rotating intermittently clockwise and anticlockwise, and a plurality of sample containers 12 containing a biological sample such as blood are mounted in the sample disk 11. The sample dispensing mechanism 10 is placed near the sample disk 11. The sample dispensing mechanism 10 can rotate clockwise and anticlockwise between the sample disk 11 and a coagulation specimen dispensing unit 43. The sample dispensing mechanism 10 sucks the sample (hereinafter also called a specimen) within a sample container 12 using a probe attached to the tip of the sample dispensing mechanism 10 and discharges the sample into a reaction container 31 on the coagulation specimen dispensing unit 43.

A plurality of reagent containers 22 corresponding to the analysis items of the automatic analysis apparatus 1 are mounted on the reagent disk 21. The coagulation reagent dispensing mechanism 20 sucks the reagent in a reagent container 22 and discharges the reagent into the reaction container 31. The coagulation reagent dispensing mechanism 20 has a built-in reagent heating mechanism 23, and the reagent sucked by the coagulation reagent dispensing mechanism 20 is heated to an appropriate temperature (a predetermined temperature) by the reagent heating mechanism 23. The reaction container 31 is a container in which the specimen and the reagent are mixed with each other and in which the mixed solution is reacted.

An arm capable of grasping a reaction container 31 is attached to the reaction container transfer mechanism 32. Moreover, the reaction container transfer mechanism 32 can move among the reaction container accommodating unit 30, the coagulation specimen dispensing unit 43 and the coagulation time measuring unit 40 and is capable of transferring and mounting the reaction container 31 to a predetermined place.

Many hollows in which the reaction containers 31 can be mounted are provided in the reaction container accommodating unit 30, and the reaction containers 31 can be inserted in the hollows.

A hollow in which the reaction container 31 can be mounted is provided in the coagulation specimen dispensing unit 43, and the reaction container 31 can be inserted in the hollow.

A coagulation time detecting unit 41 having a hollow in which the reaction container 31 can be mounted is provided on the coagulation time measuring unit 40. A reaction container 31 can be inserted in the coagulation time detecting unit 41. Moreover, a light source 42 applies light to the reaction container 31 mounted in the coagulation time detecting unit 41. The light applied from the light source 42 is scattered in the reaction container 31, and the scattered light is received with a photodiode provided in the coagulation time detecting unit 41. The analog signal of the scattered light measured is input into an A/D converter 56. Based on the digital signal input into the A/D converter, the coagulation time is measured. That is, the reaction container 31 is mounted in the coagulation time measuring unit 40, and the coagulation time of the mixed solution within the reaction container can be measured.

Next, the control system and the signal processing system in the automatic analysis apparatus 1 shown in FIG. 1 are briefly explained. The computer (control unit) 52 is connected to a specimen dispensing control unit 57, a coagulation reagent dispensing control unit 58, a reaction container transfer mechanism control unit 59 and the A/D converter 56 through an interface 50. The computer (control unit) 52 gives instructions to the control units and controls the operations. The A/D-converted photometric value is taken in by the computer (control unit) 52. That is, the computer (control unit) 52 can control the reaction container transfer mechanism, the sample dispensing mechanism and the like through the respective control units of the mechanisms.

A printer 53 for printing, a memory 55 which is a storage unit, a keyboard 51 for inputting an instruction for an operation and the like and a display 54 for displaying a picture such as a CRT display or a liquid crystal display are connected to the interface 50. The memory 55 is composed for example of a hard disk memory or an external memory. The memory 55 stores information such as analysis parameters, analysis item requests, calibration results and analysis results.

Next, the blood coagulation measurement is explained. When an operator requests analysis from the computer 52, the reaction container transfer mechanism 32 transfers and mounts the reaction container 31 on the reaction container accommodating unit 30 to the coagulation specimen dispensing unit 43. Subsequently, the sample dispensing mechanism 10 sucks the specimen used for the analysis from a sample container 12 on the sample disk 11 and discharges the specimen into the reaction container 31 on the coagulation specimen dispensing unit 43. The reaction container 31 into which the specimen has been dispensed is transferred and mounted to the blood coagulation time detecting unit 41 by the reaction container transfer mechanism 32. Then, when a reagent is discharged into the reaction container 31 on the blood coagulation time detecting unit 41 by the coagulation reagent dispensing mechanism 20, the mixed solution of the specimen and the reagent is reacted, and the blood coagulation reaction starts.

Light is applied from the light source 42 to the reaction container. The coagulation time measuring unit receives the scattered light thereof, and the A/D-converted measured value is taken in by the computer (control unit) 52 through the interface 50. The results of the measurement are output by the printer 53 or the display 54.

After the completion of the coagulation reaction, the reaction container transfer mechanism 32 grasps the reaction container 31 after the light measurement and discards the reaction container 31 at a predetermined position.

FIG. 2 is a schematic view of the automatic analysis apparatus having a blood coagulation measuring unit and an absorbance measuring unit capable of conducting biochemical measurement according to an embodiment of the invention. The automatic analysis apparatus has a structure in which the sample dispensing mechanism 10 is used for both inspection of blood coagulation and biochemical inspection. In this structure, a reaction disk 60 having a plurality of reaction cells (second reaction containers) 62 used for biochemical measurement and reagent dispensing mechanisms 61 (61(a) and 61(b)) are added to the automatic analysis apparatus shown in FIG. 1. Also, a plurality of (six units in the example of this apparatus) coagulation time detecting units 41 are provided on the coagulation time measuring unit 40. In such a structure, a reagent for inspecting blood coagulation can be sucked by the coagulation reagent dispensing mechanism 20 through the reaction disk 60 from the reagent disk (21(a) or 21(b)), and the reagent can be heated efficiently before being discharged into the reaction container 31. This is because the reaction disk 60 is kept warm at about 37° C. with a thermostatic bath.

The automatic analysis apparatus shown in FIG. 2 has two reaction container accommodating units 30. Many hollows in which the reaction containers 31 can be inserted are provided in the reaction container accommodating units 30, and empty reaction containers 31 used for blood coagulation measurement are provided in advance. Also, the reaction container accommodating units 30 have a structure which can be detached and attached. Thus, the operator can remove the reaction container accommodating units 30 and can install new reaction container accommodating units 30.

Here, the operating sequence of the reaction container transfer mechanism 32 used when blood coagulation time measurement is conducted in an embodiment of the invention is explained.

The operating sequence of the reaction container transfer mechanism 32 used when the operator registers request for analysis of a blood coagulation item and the analysis is started is shown in FIG. 3. The detailed operations of the reaction container transfer mechanism 32 are explained using FIG. 4.

Figure 4C:
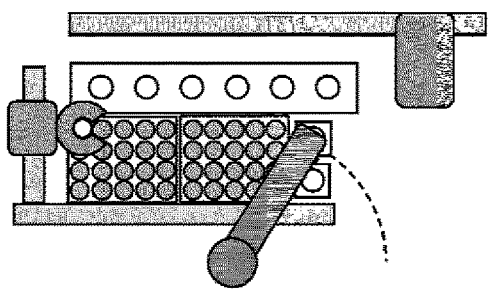
FIG. 4C A schematic view of an operation of the reaction container transfer mechanism 32 in the operating sequence shown in FIG. 3 in an embodiment of the invention.
Figure 4D:
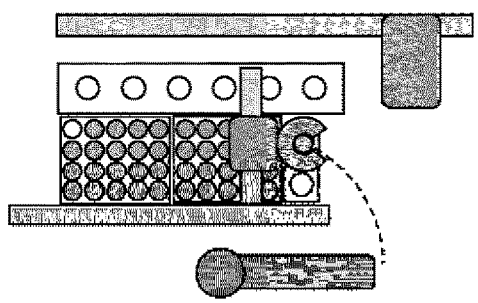
FIG. 4D A schematic view of an operation of the reaction container transfer mechanism 32 in the operating sequence shown in FIG. 3 in an embodiment of the invention.
Figure 4E:
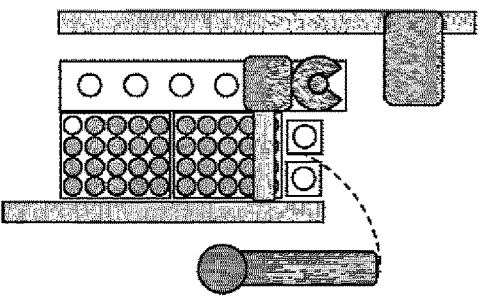
FIG. 4E A schematic view of an operation of the reaction container transfer mechanism 32 in the operating sequence shown in FIG. 3 in an embodiment of the invention.

When the operations are not conducted, the reaction container transfer mechanism 32 stays on the upper left part of the reaction container accommodating units 30, which is the reaction container transfer mechanism initial position (FIG. 3a). When the analysis is started, the reaction container transfer mechanism 32 grasps an empty reaction container 31 provided on the reaction container accommodating unit 30 (FIG. 3b and FIG. 4a) and transfers and mounts the reaction container 31 to the coagulation specimen dispensing unit 43 (FIG. 3c and FIG. 4b). Next, the reaction container transfer mechanism moves to the initial position (FIG. 3d). Then, a specimen is dispensed into the reaction container 31 on the coagulation specimen dispensing unit 43 by the sample dispensing mechanism 10 (FIG. 4c). Subsequently, the reaction container transfer mechanism 32 grasps the reaction container 31 containing the specimen on the coagulation specimen dispensing unit 43 (FIG. 3e and FIG. 4d) and transfers and mounts the reaction container 31 to the coagulation time detecting unit 41 (FIG. 3f and FIG. 4e). Then, the reaction container transfer mechanism 32 moves to the initial position (FIG. 3g), and the coagulation reagent dispensing mechanism 20 discharges a reagent into the reaction container 31 on the coagulation time detecting unit 41. The coagulation reaction is then started.

When the operator requests analysis of blood coagulation items sequentially during the analysis, the reaction container transfer mechanism 32 repeatedly conducts the operating sequence and the operations shown in FIG. 3 and FIG. 4 in the case where there is a blood coagulation time detecting unit 41 which is not used for the analysis.

In this regard, the operations of the reaction container transfer mechanism 32 are controlled by the reaction container transfer mechanism control unit 59 from the computer (control unit) 52 through the interface 50. The reaction container transfer mechanism 32 grasps an empty reaction container 31 on the reaction container accommodating units 30 and uses the reaction container 31 for the analysis in order of request for analysis and sequentially, for example along the line, from the upper left of the reaction container accommodating units 30.

The operating sequence of the reaction container transfer mechanism 32 used when all the blood coagulation time detecting units 41 are used for the measurement is shown in FIG. 5. The detailed operations of the reaction container transfer mechanism 32 are explained using FIG. 6. Whether or not all the blood coagulation time detecting units 41 are used for the measurement is determined by the computer (control unit) 52, and the computer (control unit) 52 can switch between the operating sequences shown in FIG. 3 and FIG. 5 based on the results of determination.

That is, the computer (control unit) mounts the reaction containers into which a specimen has been dispensed in the blood coagulation time measuring unit by means of the reaction container transfer mechanism until the blood coagulation time measuring unit is filled with the reaction containers. Subsequently, when the blood coagulation time measuring unit is filled with the reaction containers, the computer (control unit) transfers and mounts the reaction container containing a specimen before the measurement to the reaction container accommodating unit by means of the reaction container transfer mechanism. Subsequently, when a space for a reaction container in the blood coagulation time measuring unit becomes vacant, the computer (control unit) controls the mounting of the reaction container containing the specimen before the measurement mounted in the reaction container accommodating unit in the blood coagulation time measuring unit by means of the reaction container transfer mechanism. In this regard, the controls which are the same as those in FIG. 3 are not explained here.

Figure 6B:
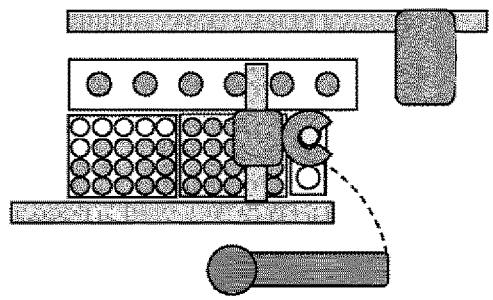
FIG. 6B A schematic view of an operation of the reaction container transfer mechanism 32 in the operating sequence shown in FIG. 5 in an embodiment of the invention.
Figure 6C:
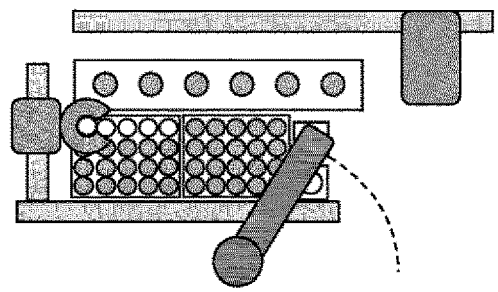
FIG. 6C A schematic view of an operation of the reaction container transfer mechanism 32 in the operating sequence shown in FIG. 5 in an embodiment of the invention.
Figure 6D:
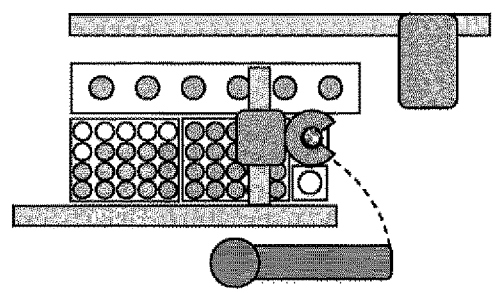
FIG. 6D A schematic view of an operation of the reaction container transfer mechanism 32 in the operating sequence shown in FIG. 5 in an embodiment of the invention.
Figure 6E:
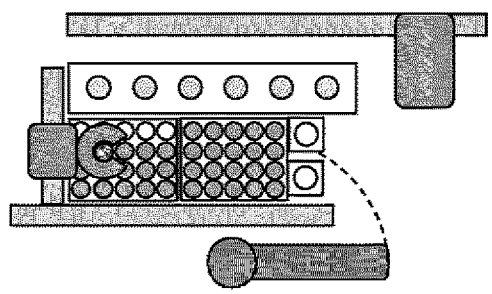
FIG. 6E A schematic view of an operation of the reaction container transfer mechanism 32 in the operating sequence shown in FIG. 5 in an embodiment of the invention.

The reaction container transfer mechanism 32 grasps an empty reaction container 31 provided on the reaction container accommodating unit 30 (FIG. 5b and FIG. 6a) and transfers and mounts the reaction container 31 to the coagulation specimen dispensing unit 43 (FIG. 5c and FIG. 6b). Then, a specimen is dispensed into the reaction container 31 on the coagulation specimen dispensing unit 43 by the sample dispensing mechanism 10 (FIG. 6c). Subsequently, the reaction container transfer mechanism 32 grasps the reaction container 35 containing the specimen on the coagulation specimen dispensing unit 43 (FIG. 5e and FIG. 6d) and transfers and mounts the reaction container 35 containing the specimen to a similar position on the reaction container accommodating unit 30 to the position where the empty reaction container 31 has been placed (FIG. 5f and FIG. 6e).

When the operator requests analysis of blood coagulation items sequentially during the analysis, the reaction container transfer mechanism 32 repeatedly conducts the operating sequence and the operations shown in FIG. 5 and FIG. 6 in the case where all the blood coagulation time detecting units 41 are used for the measurement.

Here, the similar position is not limited to the same position as the position where the empty reaction container 31 has been placed but is desirably the same position as the position where the same empty reaction container 31 has been placed. In the case where the reaction containers 31 are used regularly in order, the specimen containers before the analysis are also aligned regularly in order when the reaction containers are transferred and mounted to the same positions, and thus the operator can easily see the number of specimen containers before the analysis on the reaction container accommodating units 30.

The following effects are obtained by temporarily placing the reaction container 35 containing a specimen before the measurement on the reaction container accommodating unit 30 by the operations of the reaction container transfer mechanism 32 in this manner when all the coagulation time detecting units 41 are used for the measurement.

Even when all the coagulation time detecting units 41 in the blood coagulation time measuring unit are used for the measurement, the specimens can be prevented from staying before being dispensed, and dispensing of the specimens by the sample dispensing mechanism can be finished. Therefore, the specimens can be dispensed efficiently, and the waiting time before the exchange of the specimen containers can be shortened.

By placing the reaction container 35 containing a specimen before the measurement temporarily on the reaction container accommodating unit which is already provided in the apparatus, many coagulation time detecting units for many measurement specimens are not necessary. Thus, the device configuration can be miniaturized, and the device costs can be reduced. Moreover, because it is not necessary to newly provide an area for temporal waiting at a position different from that of the reaction container accommodating unit, the device configuration can be miniaturized, and the device costs can be reduced.

An apparatus having a reaction disk for measuring the absorbance has been explained in the embodiment, but the above effects are effects which are also obtained when there is no reaction disk. The following effects are effects which are obtained when a reaction disk for measuring the absorbance is provided and when samples for coagulation time measurement and absorbance measurement are treated by a same sample dispensing mechanism.

Even when all the coagulation time detecting units 41 are used for measurement samples, measurement can be conducted continuously without stopping the dispensing operations of the sample dispensing mechanism 10. As a result, the absorbance measurement can be conducted continuously without being restricted by the coagulation time measurement, and the inspection can be conducted efficiently. That is, even when coagulation measurement and absorbance measurement of a same specimen are both requested, the results of the absorbance measurement can be obtained early without being restricted by the coagulation time measurement. This is because it is not necessary to delay dispensing for the absorbance measurement until a coagulation time detecting unit becomes empty even when a same specimen is dispensed continuously. Moreover, the specimens can be prevented from staying before being dispensed, and the waiting time before the exchange of the specimen containers can be shortened.

To prevent contamination of the dispensed specimens from each other, the sample dispensing mechanism 10 washes the inside of the probe attached to the tip of the sample dispensing mechanism 10 with purified water after a same specimen has been dispensed. When another specimen is sucked after washing, an amount of the specimen which is more than the amount of the specimen used for the analysis is sucked as the dummy amount to prevent the specimen from being diluted with the purified water used for washing. Even when a same specimen is used, dispensing of the specimen for coagulation time measurement and dispensing of the specimen for absorbance measurement may be conducted separately. However, when another specimen is sucked between the dispensing operations, two dummy amounts are required. However, because the reaction container 35 containing a specimen before the measurement can be temporarily placed on the reaction container accommodating unit 30, dispensing of the specimen for coagulation time measurement and dispensing of the specimen for absorbance measurement can be conducted continuously by the sample dispensing mechanism 10 without discharging the sucked dummy amount sequentially in order of request for analysis by the operator without being restricted by the coagulation time measurement. The dummy amount which is excessively sucked when the specimen is dispensed can be reduced. As a result, the consumption of the sample can be reduced.

The operating sequence of the reaction container transfer mechanism 32 before the analysis has been explained above. Next, the operating sequence of the reaction container transfer mechanism 32 after the analysis is explained.

The operating sequence of the reaction container transfer mechanism 32 used when the analysis of the reaction container 31 on the coagulation time detecting unit 41 is finished is shown in FIG. 7. The detailed operations of the reaction container transfer mechanism 32 are explained using FIG. 8.

Figure 8B:
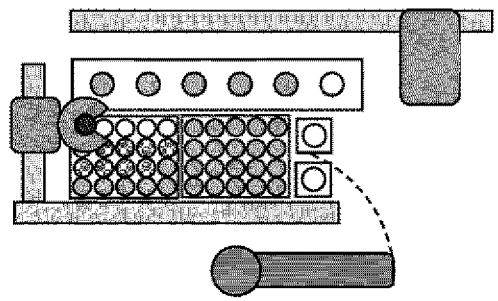
FIG. 8B A schematic view of an operation of the reaction container transfer mechanism 32 in the operating sequence shown in FIG. 7 in an embodiment of the invention.

The reaction container transfer mechanism 32 grasps the reaction container 36 containing a specimen after the analysis on the coagulation time detecting unit 41 (FIG. 7b and FIG. 8a). Then, the reaction container transfer mechanism 32 transfers and mounts the reaction container 36 containing the specimen after the analysis to the reaction container accommodating unit 30 (FIG. 7c and FIG. 8b). The reaction container 36 containing the specimen after the analysis is discarded on the reaction container accommodating unit 30 by the operations of the reaction container transfer mechanism 32. In this regard, the position on the reaction container accommodating unit 30 where the reaction container 36 containing the specimen after the analysis is discarded is the same position as the position where the reaction container 31 has been placed before the specimen has been dispensed.

By operating the reaction container transfer mechanism 32 using the reaction container accommodating unit 30 as a place for discarding the reaction container 36 containing a specimen after the analysis in this manner, an additional mechanism or an additional accommodating unit for discarding the reaction container 36 containing a specimen after the analysis is not necessary, and the apparatus can be miniaturized.

Figure 8C:
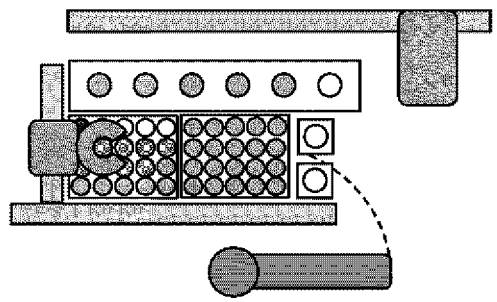
FIG. 8C A schematic view of an operation of the reaction container transfer mechanism 32 in the operating sequence shown in FIG. 7 in an embodiment of the invention.
Figure 8D:
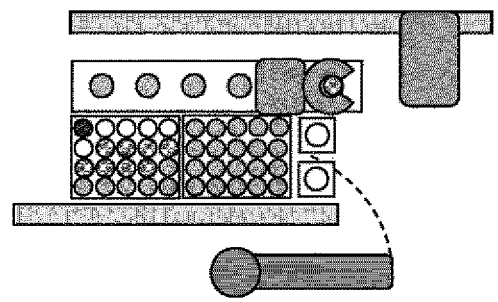
FIG. 8D A schematic view of an operation of the reaction container transfer mechanism 32 in the operating sequence shown in FIG. 7 in an embodiment of the invention.

Subsequently, when there is the reaction container 35 containing a specimen before the analysis on the reaction container accommodating unit 30, the reaction container transfer mechanism 32 grasps the reaction container 35 containing the specimen before the analysis mounted on the reaction container accommodating unit 30 (FIG. 7d and FIG. 8c). Then, the reaction container transfer mechanism 32 transfers and mounts the reaction container 35 containing the specimen before the analysis to the empty coagulation time detecting unit 41 (FIG. 7e and FIG. 8d), and coagulation reaction is measured. In this regard, the reaction container transfer mechanism 32 transfers and mounts the reaction container 35 containing a specimen before the analysis to the coagulation time detecting unit 41 in order of requested item for analysis.

As long as there is a specimen after the analysis on the blood coagulation time detecting unit 41, the reaction container transfer mechanism 32 repeatedly conducts the operating sequence and the operations shown in FIG. 7 and FIG. 8. When there is no reaction container containing a specimen before the analysis on the reaction container accommodating units 30, however, the sequence shown in FIGS. 7(d) and (e) is skipped.

Next, the operating sequence of the reaction container transfer mechanism 32 used when there is a reaction container containing an emergency specimen is explained.

The operating sequence of the reaction container transfer mechanism 32 used when the analysis of the reaction container 31 on the coagulation time detecting unit 41 is finished and when there is the reaction container 37 containing an emergency specimen on the reaction container accommodating unit 30 is shown in FIG. 9. The detailed operations of the reaction container transfer mechanism 32 are explained using FIG. 10.

That is, the computer (control unit) transfers and mounts the reaction container containing an emergency specimen before the measurement to the reaction container accommodating unit by means of the reaction container transfer mechanism when the blood coagulation time measuring unit is filled with the reaction containers. Subsequently, the computer (control unit) controls the transferring and mounting of the reaction container containing the emergency specimen mounted in the reaction container accommodating unit to the blood coagulation time measuring unit by means of the reaction container transfer mechanism prior to the reaction containers containing a specimen before the measurement which are already mounted in the reaction container accommodating units when a space for a reaction container in the blood coagulation time measuring unit becomes vacant. In this regard, the operations of from dispensing of the emergency specimen to transferring and mounting to the reaction container accommodating unit by the reaction container transfer mechanism 32 are conducted in similar manners as those in FIG. 5 and FIG. 6(a) to FIG. 6(e).

Figure 10B:
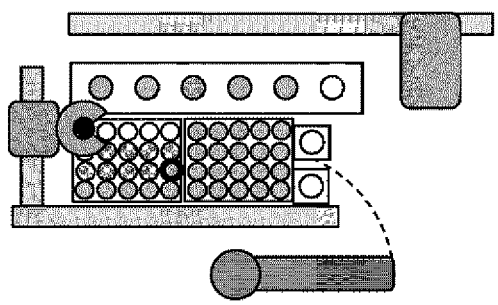
FIG. 10B A schematic view of an operation of the reaction container transfer mechanism 32 in the operating sequence shown in FIG. 9 in an embodiment of the invention.
Figure 10C:
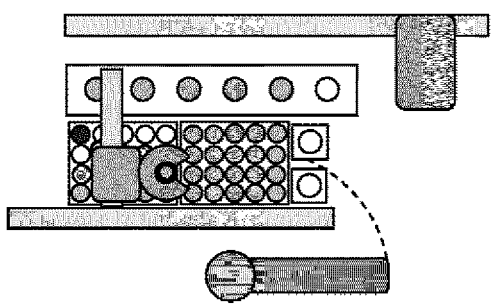
FIG. 10C A schematic view of an operation of the reaction container transfer mechanism 32 in the operating sequence shown in FIG. 9 in an embodiment of the invention.
Figure 10D:
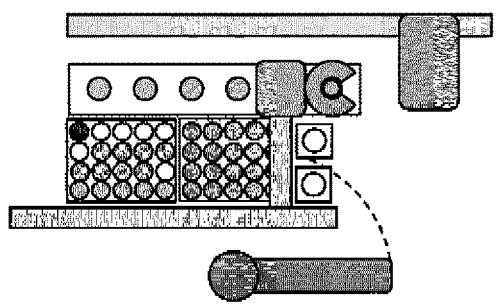
FIG. 10D A schematic view of an operation of the reaction container transfer mechanism 32 in the operating sequence shown in FIG. 9 in an embodiment of the invention.

The reaction container transfer mechanism 32 grasps the reaction container 36 containing a specimen after the analysis on a coagulation time detecting unit 41 (FIG. 9b and FIG. 10a) and transfers and discards the reaction container 36 containing the specimen after the analysis on the reaction container accommodating unit 30 (FIG. 9c and FIG. 10b). Subsequently, the reaction container transfer mechanism 32 grasps the reaction container 37 containing the emergency specimen mounted on the reaction container accommodating unit 30 preferentially regardless of the order of request for analysis (FIG. 9d and FIG. 10c). Then, the reaction container transfer mechanism 32 transfers and mounts the reaction container 37 containing the emergency specimen to the empty coagulation time detecting unit 41 (FIG. 9e and FIG. 10d), and coagulation reaction is measured. When there is an empty coagulation time detecting unit 41, however, the reaction container 37 containing the emergency specimen is transferred and mounted to the coagulation time detecting unit from the coagulation specimen dispensing unit without through the reaction container accommodating unit by the operating sequence and the operations shown in FIG. 3 and FIG. 4.

As long as there is a reaction container 37 containing an emergency specimen on the reaction container accommodating unit 30, the reaction container transfer mechanism 32 repeatedly conducts the operating sequence and the operations shown in FIG. 9 and FIG. 10. When there is no reaction container after the analysis, however, the sequence shown in FIGS. 9(b) and (c) is skipped.

When there is an empty coagulation time detecting unit 41, however, the reaction container containing the emergency specimen before the measurement is not mounted in the reaction container accommodating unit but is mounted in the coagulation time detecting unit, and the measurement of the reaction container is conducted. On the other hand, when all the coagulation time detecting units 41 are filled with the reaction containers, the reaction container containing the emergency specimen before the measurement is mounted in the reaction container accommodating unit, and the operating sequence shown in FIG. 9 is conducted.

Next, a screen displayed on the display 54 is explained.

During the operations of the reaction container transfer mechanism 32 for transferring and mounting a reaction container 31, information such as the position on the reaction container accommodating unit 30 where the reaction container 35 containing the specimen before the analysis is placed, the position on the reaction container accommodating unit 30 where the reaction container 36 containing the specimen after the analysis is discarded, the results of the measurement and the information on an alarm is stored in the memory 55 through the interface 50.

As shown in FIG. 11, the operator can display the information on the reaction containers 31 on the reaction container accommodating units 30 recorded in the memory 55 on the display 54. The indication of reaction container accommodating units 1 and 2 in FIG. 11 corresponds to the physical arrangement of the reaction container accommodating units 30. Moreover, the respective positions corresponding to the reaction containers are displayed distinguishably so that the statuses such as "no reaction container", "an unused reaction container", "a reaction container containing a general specimen", "a reaction container containing an emergency specimen" and "a reaction container after the analysis" can be distinguished visually. Furthermore, by selecting any reaction container 31 on the reaction container accommodating units 30 displayed on the display 54 using the computer (control unit) 52, the operator can check the specimen information on the specimen dispensed into the reaction container 31 (for example, the specimen number, the measurement item and the state of measurement of the reaction container, as well as the results of the measurement and the information on an alarm after the analysis). For example, even if a trouble arises during the analysis or after the analysis, the place where the specimen with unusual measurement results is discarded can be checked on the display 54 because the information on an alarm is added. In this regard, the specimen information may be a part of the information cited above.

As a result, the operator can visually check the state of a specimen with a trouble after the reaction. The operator can also use the information to examine the cause of the unusual measurement results as to whether the unusual measurement results are due to mixing of air bubbles or a foreign matter.

Moreover, when the operator selects any reaction container 36 containing a specimen after the analysis displayed on the display 54 through the computer (control unit) 52, the reaction container transfer mechanism 32 can grasp the selected reaction container 36 containing the specimen after the analysis on the reaction container accommodating unit 30 and transfer and mount the reaction container 36 to the reaction container checking unit 33 (see FIG. 2). The reaction container checking unit 33 is placed at a position which is easily checked visually by the operator. Because the reaction container 36 containing the specimen after the analysis can be moved to a position which is easily checked visually by the reaction container transfer mechanism 32, the operator can easily check the state of the specimen within the reaction container 31 after the analysis.

FIG. 12 is a schematic view of the automatic analysis apparatus having a blood coagulation measuring unit and an absorbance measuring unit capable of conducting biochemical measurement according to an embodiment of the invention. As shown in FIG. 12, the reaction container discarding unit 34 for discarding and accommodating the reaction container 35 containing a specimen after the analysis may be provided separately from the reaction container accommodating units 30 in the automatic analysis apparatus shown in FIG. 2. In this regard, the reaction container discarding unit 34 has a structure which can be detached and attached, and the operator can attach and remove the reaction container discarding unit 34. Although a space for the reaction container discarding unit 34 is necessary in this case, because the reaction container containing a specimen before the measurement can be placed temporarily in the reaction container accommodating unit 30, the device configuration can be miniaturized, or the device costs can be reduced.

The embodiments have been explained above.

It has been explained that the computer (control unit) 52 controls the transferring and mounting of the reaction container into which a specimen has been dispensed to the reaction container accommodating unit by means of the reaction container transfer mechanism. As a result, when the reaction container which is transferred and mounted is the reaction container containing a specimen before the measurement, a reduction in the size corresponding to the area used exclusively for waiting, prevention of a decrease in the efficiency of dispensing or the like can be achieved. When the reaction container is the reaction container after the measurement, a reduction in the size corresponding to the area used exclusively for discarding or the like can be achieved. Accordingly, an automatic analysis apparatus which is capable of miniaturizing device configuration and reducing device costs can be provided in both cases.

When the reaction container which is moved and mounted is a reaction container containing a specimen before the measurement and when a reaction container containing an emergency specimen is mounted in a reaction container accommodating unit, the computer (control unit) 52 desirably controls the transferring and mounting of the reaction container containing the emergency specimen mounted in the reaction container accommodating unit preferentially to the blood coagulation time measuring unit by means of the reaction container transfer mechanism. As a result, the above effects are obtained, and the emergency specimen can be measured preferentially.

The computer (control unit) 52 desirably controls the storage of the position of the reaction transferred and mounted to the reaction container accommodating unit by means of the reaction container transfer mechanism and the information on the specimen within the mounted reaction container in an internal or external memory of the apparatus. As a result, the operator can draw the information on the reaction container mounted in the accommodating unit. Moreover, the operator can check the specimen information corresponding to the position because a display which displays the position and the information on the specimen recorded in the memory.

A reaction container checking unit to which the reaction container mounted in the reaction container accommodating unit is transferred and mounted is desirably further provided, and when the operator selects the reaction container on the reaction container accommodating unit displayed on the display, the computer (control unit) 52 desirably controls the transferring and mounting of the selected reaction container from the reaction container accommodating unit to the reaction container checking unit by means of the reaction container transfer mechanism. As a result, the operator can easily check the state of the specimen within the reaction container 31 after the analysis.

The reaction container discarding unit for discarding the reaction container can be provided, and when the measurement of the mixed solution within the reaction container mounted in the blood coagulation time measuring unit is finished, the computer (control unit) 52 can control the transferring and discarding of the reaction container after the measurement to the reaction container discarding unit by means of the reaction container transfer mechanism. The operator can attach and remove the reaction container discarding unit independently from the reaction container accommodating units. Also in this case, the computer (control unit) 52 desirably controls the transferring and mounting of the reaction container containing a specimen before the measurement mounted in the reaction container accommodating unit to the blood coagulation time measuring unit by means of the reaction container transfer mechanism. An emergency specimen can be measured preferentially also in this case.

A reaction disk having second reaction containers for biochemical measurement is desirably provided; the sample dispensing mechanism desirably dispenses a specimen into the second reaction container; and when a same specimen is dispensed into the reaction container and the second reaction container by the sample dispensing mechanism, the computer (control unit) 52 desirably controls the suction of an amount of the specimen which is the sum of an amount of the specimen used for the analysis and a dummy amount that is not used for the analysis by means of the sample dispensing mechanism and the discharge of the same specimen into the reaction container and the second reaction container without the discharge of the sucked dummy amount. As a result, the consumption of the sample can be reduced.

Although examples using six coagulation time detecting units have been explained in the embodiments, the number may be any number which balances with the performance of the apparatus. However, the device configuration cannot be miniaturized or the device costs cannot be reduced when there are too many coagulation time detecting units. Thus, the number as a rough target is desirably 10 or less.

Both a reaction container after the measurement and a reaction container containing a specimen before the measurement are handled in the embodiments, but only one thereof may be transferred and mounted to the reaction container accommodating unit by the reaction container transfer mechanism.

Examples of an automatic analysis apparatus having a reaction disk used for biochemical measurement have been explained in the embodiments, but the reaction disk is not an essential component. When the reaction disk is provided, the absorbance can be measured continuously in biochemical measurement without being restricted by coagulation time measurement, and the inspection can be conducted efficiently.

Examples using the sample disk 11 have been explained in the embodiments, but the invention can be applied to a rack-type automatic analysis apparatus in which the specimen container containing a specimen is mounted on a rack and analyzed.

The coagulation time detecting units 41 explained above are detecting units using scattered light, but a known detecting unit which detects transmitted light or consistency instead of detecting scattered light may be applied to the blood coagulation time measuring unit.

REFERENCE SIGNS LIST

1 . . . automatic analysis apparatus, 10 . . . sample dispensing mechanism, 11 . . . sample disk, 12 . . . sample container, 20 . . . coagulation reagent dispensing mechanism, 21 . . . reagent disk, 22 . . . reagent container, 23 . . . reagent heating mechanism, 30 . . . reaction container accommodating unit, 31 . . . reaction container, 32 . . . reaction container transfer mechanism, 33 . . . reaction container checking unit, 34 . . . reaction container discarding unit, 35 . . . reaction container containing specimen before analysis, 36 . . . reaction container containing specimen after analysis, 37 . . . reaction container containing emergency specimen, 40 . . . coagulation time measuring unit, 41 . . . coagulation time detecting unit, 42 . . . light source, 43 . . . coagulation specimen dispensing unit, 50 . . . interface, 51 . . . keyboard, 52 . . . computer (control unit), 53 . . . printer, 54 . . . display, 55 . . . memory, 56 . . . A/D converter, 57 . . . specimen dispensing control unit, 58 . . . reagent dispensing control unit, 59 . . . reaction container transfer mechanism control unit, 60 . . . reaction disk, 61 . . . reagent dispensing mechanism, 62 . . . reaction cell (second reaction container)

The invention claimed is:

1. An automatic analysis apparatus, comprising:
a blood coagulation timer for mounting a reaction container therein to measure a coagulation time of a mixed solution within the reaction container;
a sample dispenser for dispensing a specimen into the reaction container, the reaction container being for mixing the specimen and a reagent with each other therein and for reacting the mixed solution therein;
a coagulation specimen dispenser for housing the reaction container when the specimen is dispensed;
a reaction container housing for accommodating a plurality of reaction containers, among them the reaction container to be provided to the blood coagulation timer, the reaction container housing being spaced apart from the coagulation specimen dispenser;
a reaction container carrier for grasping the reaction container and transferring the reaction container to the blood coagulation timer; and
a controller configured to control the reaction container carrier,
wherein the controller is configured to control the transferring and mounting of the reaction container, into which the specimen is dispensed, to the reaction container housing by means of the reaction container carrier, and
wherein the transferring of the reaction container occurs from the coagulation specimen dispenser.

2. The automatic analysis apparatus according to claim 1, wherein the controller controls the transferring and mounting of the reaction container containing an unused specimen mounted in the reaction container housing to the blood coagulation timer by means of the reaction container carrier.

3. The automatic analysis apparatus according to claim 2, wherein when the reaction container containing an emergency specimen is mounted in the reaction container housing, the controller controls the transferring and mounting of the reaction container containing the emergency specimen mounted in the reaction container housing preferentially to the blood coagulation timer by means of the reaction container carrier.

4. The automatic analysis apparatus according to claim 1, wherein the reaction container housing has a shape capable of accommodating the plurality of reaction containers, and
the controller controls the storage of the position of the reaction container transferred and mounted to the reaction container housing by means of the reaction container carrier and information on the specimen within the mounted reaction container in an internal or external memory of the apparatus.

5. The automatic analysis apparatus according to claim 4, wherein further having a display which displays the position and the information on the specimen recorded in the memory.

6. The automatic analysis apparatus according to claim 5, further having a reaction container checking unit to which a reaction container mounted in the reaction container housing is transferred and mounted,
wherein when an operator selects the reaction container on the reaction container housing displayed on the display, the controller controls the transferring and mounting of the selected reaction container from the reaction container housing to the reaction container checking unit by means of the reaction container carrier.

7. The automatic analysis apparatus according to claim 1, further having a reaction container discarding unit for discarding the reaction container,
wherein when the measurement of the mixed solution within the reaction container mounted in the blood coagulation timer is finished, the controller controls such that the reaction container after the measurement is transferred to the reaction container discarding unit by means of the reaction container carrier.

8. The automatic analysis apparatus according to claim 7, wherein the controller controls the transferring and mounting of the reaction container containing an unused specimen mounted in the reaction container housing to the blood coagulation timer by means of the reaction container carrier.

9. The automatic analysis apparatus according to claim 8, wherein when the reaction container containing an emergency specimen is mounted in the reaction container housing, the controller controls the transferring and mounting of the reaction container containing the emergency specimen mounted in the reaction container housing preferentially to the blood coagulation timer by means of the reaction container carrier.

10. The automatic analysis apparatus according to claim 1, further having a reaction disk having a second reaction container for biochemical measurement,
wherein the sample dispenser dispenses a specimen into the second reaction container, and
when a same specimen is dispensed into the reaction container and the second reaction container by the sample dispenser, the controller controls the suction of an amount of the specimen which is the sum of an amount of the specimen used for the analysis and a dummy amount that is not used for the analysis by means of the sample dispenser and the discharge of the same specimen into the reaction container and the second reaction container without the discharge of the sucked dummy amount.

11. An automatic analysis apparatus, comprising:
a blood coagulation timer for mounting a reaction container therein to measure a coagulation time of a mixed solution within the reaction container;
a sample dispenser for dispensing a specimen into the reaction container, the reaction container being for mixing the specimen and a reagent with each other therein and for reacting the mixed solution therein;
a coagulation specimen dispenser for housing the reaction container when the specimen is dispensed;
a reaction container housing for accommodating a plurality of reaction containers, among them the reaction container to be provided to the blood coagulation timer, the reaction container housing being spaced apart from the coagulation specimen dispenser;
a reaction container carrier for grasping the reaction container and transferring the reaction container to the blood coagulation timer; and
a controller configured to control the reaction container carrier,
wherein the controller is configured to control the transferring and mounting of the reaction container, into which the specimen is dispensed, to the reaction container housing by means of the reaction container carrier,
wherein the transferring of the reaction container occurs from the coagulation specimen dispenser, wherein the controller controls
- the mounting of the reaction containers, into which a specimen is dispensed, in the blood coagulation timer by means of the reaction container carrier until the blood coagulation timer is filled with the reaction containers,
- the transferring and mounting of a reaction container containing a specimen before the measurement to the reaction container housing by means of the reaction container carrier when the blood coagulation timer is filled with the reaction containers, and
- the mounting of the reaction container containing the specimen before the measurement mounted in the reaction container housing in the blood coagulation timer by means of the reaction container carrier when a space for a reaction container in the blood coagulation timer becomes vacant, and wherein when the measurement of the mixed solution within the reaction container mounted in the blood coagulation timer is finished, the controller controls the transferring and mounting of the reaction container after the measurement to the reaction container housing by means of the reaction container carrier.

12. The automatic analysis apparatus according to claim 11,
wherein the controller controls
- the transferring and mounting of the reaction container containing an emergency specimen before the measurement to the reaction container housing by means of the reaction container carrier when the blood coagulation timer is filled with the reaction containers, and
- the transferring and mounting of the reaction container containing the emergency specimen mounted in the reaction container housing to the blood coagulation timer by means of the reaction container carrier prior to the reaction containers containing a specimen before the measurement which are already mounted in the reaction container housing when a space for a reaction container in the blood coagulation timer becomes vacant.

* * * * *